(12) United States Patent
Soma et al.

(10) Patent No.: US 11,357,938 B2
(45) Date of Patent: Jun. 14, 2022

(54) RESPIRATORY ACOUSTIC DEVICE

(71) Applicant: ACOUSTIC INNOVATIONS CO., LTD., Fuchu (JP)

(72) Inventors: Ippei Soma, Fuchu (JP); Hawkins Sanford Elliot, Fuchu (JP)

(73) Assignee: Acoustic Innovations Co., Ltd., Tokyo (JP)

( * ) Notice: Subject to any disclaimer, the term of this patent is extended or adjusted under 35 U.S.C. 154(b) by 0 days.

(21) Appl. No.: 16/761,791

(22) PCT Filed: Oct. 15, 2018

(86) PCT No.: PCT/JP2018/038267
§ 371 (c)(1),
(2) Date: May 5, 2020

(87) PCT Pub. No.: WO2019/093073
PCT Pub. Date: May 16, 2019

(65) Prior Publication Data
US 2021/0178094 A1 Jun. 17, 2021

(30) Foreign Application Priority Data
Nov. 7, 2017 (JP) .............................. JP2017-214937

(51) Int. Cl.
*A61M 16/00* (2006.01)
*A63B 23/18* (2006.01)
*A61M 16/06* (2006.01)

(52) U.S. Cl.
CPC ........ *A61M 16/0006* (2014.02); *A61M 16/06* (2013.01); *A63B 23/18* (2013.01)

(58) Field of Classification Search
CPC .......... A61M 16/0006; A61M 16/0003; A61M 16/00; A61M 16/0009; A61M 16/0012;
(Continued)

(56) References Cited

U.S. PATENT DOCUMENTS 4,240,320 A * 12/1980 Pellerite ................. G10D 7/026
84/384
4,533,137 A * 8/1985 Sonne ..................... A63B 23/18
128/207.16
(Continued)

FOREIGN PATENT DOCUMENTS

CN 2199794 Y 6/1995
CN 2629683 Y 8/2004
(Continued)

OTHER PUBLICATIONS

Arai Laboratory, "Helmholtz Resonance", 2013, Sophia University, Whole Page (Year: 2013).*
(Continued)

*Primary Examiner* — Joseph D. Boecker
*Assistant Examiner* — Brian T Khong
(74) *Attorney, Agent, or Firm* — Pyprus Pte Ltd; George D. Liu (57) ABSTRACT

A respiratory acoustic device is provided that is easy to operate and transport. The device delivers vibrations artificially to the lungs and airways to fluidize mucus adhering to the airways and promote its discharge. A respiratory acoustic device 1 is provided with a housing 10, and a mouthpiece 20 that is in communication with the housing 10. The housing 10 has a reflecting end 12 for reflecting air that has been blown in from the mouthpiece 20 and an open end 13 through which air that has been blown in from the mouthpiece 20 can escape. If a sudden exhalation such as a cough is blown into the housing 10 through the mouthpiece 20, the device causes the noise due to said exhalation to resonate with the oral and lower airway cavities, and vibrate the user's lungs and airways with the low frequency acoustic shock waves generated therein.

6 Claims, 5 Drawing Sheets

(58) Field of Classification Search
CPC ............... A61M 16/06; A61M 16/049; A61M 16/0488; A63B 21/00196; A63B 21/00069; A63B 23/18; G10D 7/02; G10D 7/00; G10D 7/026; A61H 31/00; A63H 33/40
See application file for complete search history.

(56) References Cited

U.S. PATENT DOCUMENTS

| | | | | |
|---|---|---|---|---|
| 4,550,637 | A * | 11/1985 | Drelinger | G10D 7/026 84/384 |
| 4,739,987 | A * | 4/1988 | Nicholson | A63B 23/18 128/207.16 |
| 5,357,975 | A * | 10/1994 | Kraemer | A61B 5/087 600/538 |
| 5,862,802 | A * | 1/1999 | Bird | A61M 16/00 128/204.18 |
| 5,890,998 | A * | 4/1999 | Hougen | A61M 16/0006 482/13 |
| 5,893,361 | A * | 4/1999 | Hughes | A61M 16/021 128/200.24 |
| 6,083,141 | A * | 7/2000 | Hougen | A61M 16/0006 128/202.16 |
| 6,190,337 | B1 * | 2/2001 | Nedwell | A61H 23/0236 600/587 |
| 2004/0255754 | A1 * | 12/2004 | Richter | G10D 7/026 84/380 R |
| 2007/0272071 | A1 * | 11/2007 | Parmenon | G10D 7/026 84/384 |
| 2009/0159062 | A1 * | 6/2009 | Bohman | A63F 9/02 124/62 |
| 2014/0190481 | A1 * | 7/2014 | Jam | A61M 16/024 128/203.12 |
| 2015/0360079 | A1 | 12/2015 | Keller et al. | |
| 2016/0121062 | A1 * | 5/2016 | Davenport | A61H 23/02 601/47 |
| 2018/0308459 | A1 * | 10/2018 | Lakat | G10D 9/02 |

FOREIGN PATENT DOCUMENTS

| | | | | |
|---|---|---|---|---|
| CN | 102472661 | A | 5/2012 | |
| GB | 2196858 | A * | 5/1988 | ....... A63B 21/00196 |
| GB | 2196858 | A | 5/1988 | |
| JP | 2007-504505 | A | 3/2007 | |
| JP | 4025293 | B | 12/2007 | |
| KR | 20010017069 | A | 3/2001 | |
| WO | WO2015017416 | A1 | 2/2015 | |

OTHER PUBLICATIONS

International Search Report of International Patent Application No. PCT/JP2018/038267 completed Nov. 12, 2018 and dated Nov. 27, 2018 (4 pages).
Written Opinion of International Patent Application No. PCT/JP2018/038267 completed Nov. 12, 2018 and dated Nov. 27, 2018 (3 pages).
Notice of Reasons for Refusal of Japanese Application No. 2017-214937 dated Jun. 10, 2020 (3 pages).
Office Action of Chinese Application No. 201880071946.3 dated Mar. 8, 2021 (7 pages).
Supplementary Search Report and Search Opinion of European Application No. 18875552.4 dated Jul. 12, 2021 (6 pages).

* cited by examiner

$$f = \frac{c}{2\pi}\sqrt{\frac{S}{Vl}}$$

Figure 5

RESPIRATORY ACOUSTIC DEVICE

TECHNICAL FIELD

The present invention relates to the respiratory acoustic device to promote the removal of the mucus stacked to the human lower airway. In detail description, the respiratory acoustic device of present invention is to vibrate the airway and lungs of the user by a low frequency acoustic shockwave generated by the resonation between noise of a rapid exhalation, i.e. a cough, and the cavity formed by the oral cavity and the lower respiratory tract.

BACKGROUND ART

Human lower airway provides natural means to remove mucus contained therein, which is embedded minute cilia vibrating at 16-25 Hz (specifically, around 18 Hz). The cilia will move out the mucus from the airway which catches alien substances and bacteria which come into the airway from outside. The cilia play a role to keep the airway clean and to prevent infectious diseases and mucus obstruction.

The vibration frequency of these cilia is known as CBF, Cilia Beating Frequency, and is said to be the same frequency in most mammals from a mouse to an elephant. As for airway mucus, its phase shifts from a viscous fluid to liquid, and to thinner secretion dramatically by being applied the vibration of frequency of 16-25 Hz and then it will be removed to the outside of airway. In other words, the cilia liquify mucus by vibration generated from its periodic vibration and cleans airway by carrying mucus out by its motion to the oral side. Because the mucus should be carried up against gravity from lower airway to pharynx, some viscosity is necessary, but mucus can be removed more easily if its liquidity is high. Normally, removed airway mucus is swallowed unconsciously. In a healthy person, this health defense system by mucus and cilia functions smoothly and it is said that a human removes and swallows airway mucus approximately 60-100 ml a day.

However, there are cases that this natural health defense system loses its normal function because of the malfunction caused from age or from the illness, or because of increased inflammatory reaction from allergy, air dust or a disease. For example, there is a case that respiratory functions have trouble by airway obstruction which is caused by the lowered mobility of cilia which resulted in lack of phase shift of mucus, and is caused by the excessive airway mucus production, resulting in lowered mobilization. In which case, lowers the respiratory function due to the mucus obstructing the airway. It would be possible to improve the clearance of the obstructed airway if we can artificially generate a vibration into the airway, and obtain a necessary phase shift to mucus to assist the efficiency of cilia, and promote mucus removal.

In addition, the doctors may have to sample a sputum from the patient for the purpose of diagnosis of diseases. But a patient cannot expectorate sputum with a good quality for diagnosis if there is not a mucus originated from lower respiratory tract of enough volume with good mobility near the pharynx. If a patient cannot expectorate a good quality sputum sample at the hospital visit, the patient needs to re-visit the hospital after collecting the sample at their own home when the sputum is available or there is a case of even taking the more invasive method by collecting gastric juice or bronchoscope inspection. It can certainly reduce the burden on the patient by shortening the time of diagnosis or by avoiding the invasive methods if a good sputum sample collection could be achieved at the hospital visit with shorter time by inducing mucus of enough volume to near the pharynx by artificially generate a vibration into the airway.

Furthermore, a living body produces a rapid exhalation called "a cough", consciously or reflectively, to improve the obstruction of the airway. A cough is an exercise which consumes much energy and it is said that 2 kcal of energy will be consumed by a single cough. Also, it is said that the airflow speed generated by a cough could be up to more than 160 km/h.

However, the effect of a cough is limited to applying force from the surface of the mucus layer causing it to detach by shrinking the airway and rapidly exhaling the air therein by this shrinkage. Thus, we have to say that the effect of a cough may not be enough to remove the hard, viscous mucus out, in order to improve the airway obstruction, as its power only reaches to the surface of the mucus layer and not changing the viscosity of the mucus. There are many cases of the exacerbation because coughs were unable to remove the mucus and only took away patient's strength by the continuous excessive coughing.

CITATION LIST

Patent Literature

Patent Literature 1: Japanese Patent no. 4025293

SUMMARY OF INVENTION

Technical Problem

One of the conventional arts to promote the removal of the mucus is to artificially vibrate the lower airway of the patient by applying a pulse of air pressure to the lower airway from the mouth. However, the pulse only reaches to the part where the air cavity is continuously connected from the mouth and thus cannot bring an effect to the lower part of the thick mucus layer nor the inner airway beyond the point of obstruction. Also, the devices which works by the exhalation of the patient require rather high exhalation pressure to produce enough pulses and thus the applicable patients were quite limited. Furthermore, the machine which applies an artificially generated air pressure pulses into the airway had a risk to damage the weak air pouch of the lung s with unexpectedly produced high air pressure.

The other conventional art to let the lungs vibrate artificially is, to produce approximately 18 Hz low frequency sound by blowing air into the housing to vibrate the reed therein.

However, there existed a weakness in this art, as it could not be effective when a patient could not vibrate the reed because of low exhalation pressure or inappropriate blowing technique as this art generated a low frequency sound shockwave by generating sound by vibrating the reed and produce a resonation with the cavity of the body. Even from a technical point of view, a certain loss of the energy and the additional part separation are required because this previous art converts the energy of an exhalation into the moving energy of the reed before coupling it finally into the acoustic energy.

In addition, this previous art requires the length of about 30 cm to make the reed generate sounds of lower frequency band, and this size restriction sometimes limits the pediatric use and easy carriage.

Therefore, the present invention is aimed to offer a respiratory acoustic device to liquify the lower airway secretions and then promote its removal by means of applying vibration into the airway and lungs which is easier to use for wider age groups to properly demonstrate the appropriate effect, and which is smaller and more portable size.

Solution to Problem

The inventors of the present invention found out after their diligent study to solve the above issue, it is possible to remove the mucus by changing the viscosity of mucus in the airway and lungs by changing the viscosity of mucus with a low frequency acoustic shockwave applied by the Helmholtz resonation between noise produced from a rapid exhalation, i.e. a cough, and the cavity formed by oral cavity and lower respiratory tract. The device to realize the effect, they developed a device which has the design of a hollow housing with a mouthpiece inlet and the parts of the housing to be the reflect end and the open end to let inputted exhalation to reflect at the reflect end of the housing and exit from the open end. The invention is completed by finding this design, which allow anyone to easily function and which can limit the overall device size to be small and portable. In detail, the present invention contains the following embodiments.

The present invention is about the respiratory acoustic device 1. The respiratory acoustic device 1 is a device to apply vibration into the airway and lungs of the user by a low frequency acoustic shockwave generated by Helmholtz resonation between the noise of a rapid exhalation, i.e. a cough, and the cavity formed by oral cavity and lower respiratory tract. The respiratory acoustic device 1 has a housing 10 and a mouthpiece 20. The housing 10 and the mouthpiece 20 can be integrally formed of a single material or structured with different materials. The housing 10 has a hollow space 11. The mouthpiece 20 has a air passage 21 where is continuously connected with the hollow space 11 of the housing 10. The housing 10 has a reflection end 12 and an open end 13. The reflection end 12 of the housing 10 reflects the airflow inputted from mouthpiece 20. The "reflection end" means the end part where the fixed end reflection of the air pressure occur. It is possible that the reflection end 12 to be a completely closed end part or to be an end part with more than a couple of openings being formed. On the other hands, the open end 13 of the housing 10 should not have any component to obstruct the airflow at the edge section and exit the airflow which was blown in from mouthpiece 20. This structure causes at least a part of the airflow blown in from mouthpiece 20 will exit from open end 13 after being reflected at the reflection end 12 of the housing 10 and this generates Helmholtz resonation between the noise of a cough itself occurred at the airway of the user and of turbulence or vortex of the airflow occurred in the housing 10, and the cavity formed by the oral cavity and lower respiratory tract. Note that the "Helmholtz resonation" means an effect that generates sound by the resonation (oscillation) which happens when the air within the container with the opening acts as a spring. For the device of the present invention, the oral cavity and lower respiratory tract will act as above said "container".

It is desirable that the housing 10 of the respiratory acoustic device 1 by the present invention, is in a tubular form. "Tubular form" means a form of a long narrow form which has two ends, and the hollow space 11 is penetrating from one end to the other. Tubular form includes the round tube shape, triangle tube shape, square tube shape and the other polygonal tube shapes. Additionally, the tubular housing 10 is desirable to be linearly formed but it could be curved or bent. One end of the tubular housing 10 will be reflection end 12 and the other end will be open end 13. It is desirable that the mouthpiece 20 to be located between reflection end 12 and open end 13 of the housing 10.

It is desirable that the size of the inner dimension of the air passage 21 of the mouthpiece 20 of the respiratory acoustic device 1 by the present invention to be between 0.64 to 9 cm². By keeping the size of the inner dimension of the mouthpiece relatively large, it will be easier to infuse the rapid exhalation, i.e. cough into the housing 10. The present invention is expected to uses the user's cough as energy to efficiently create low frequency acoustic shock waves, therefore the inner dimension of mouthpiece 20 should be as large as stated above.

It is desirable that the dimension size of the air passage 21 of the mouthpiece 20 is identical to the hollow space 11 of the housing 10 of the respiratory acoustic device 1. In other words, it is desirable that the dimensional shape of the air passage 21 of the mouthpiece 20 and the hollow space 11 of the housing 10 are the same and their dimensional areas are approximately equal. Note that the word "identical dimension size" means that the inner dimensional area difference of those two are within +/−5%.

It is desirable that the size of the respiratory acoustic device 1 of the present invention, an inner dimension area of the open end 13 of the housing 10: S[cm²] and the total length of the passage in the device until the airflow blown from the mouthpiece 20 is reflected at the reflection end 12 and outputted from the open end 13: l[cm], is designed to meet the following formula.

$$f = \frac{c}{2\pi}\sqrt{\frac{S}{Vl}} \quad \text{[formula]}$$

f: sound frequency 16-25 Hz, c: sonic speed 35000 cm/s, and V: lung total capacity 1500-9000 ml.

Designing the device in this way of inner dimensional area S of the open end 13 of the housing 10 and length of the air passage 1, it will be possible to efficiently generate a low frequency sound shockwave of 16-25 Hz by the Helmholtz resonation. By applying shockwave of this range of frequency into the airway, the promotion of the mucus out from airway will be possible while the airway mucus would change its phase from a viscous body to a liquid, thinner secretion. To be noted, the total lung capacity V changes between user to user of the respiratory acoustic device 1. For example, the total lung capacity V for an adult male is normally 5500-6000 ml, an adult female is 4500-5500 ml, and children are 1500-2500 ml.

The reflection end 12 of the housing 10 of the respiratory acoustic device 1 of present invention can be without any opening, or can be with more than a couple openings or can be with a mechanism to regulate the opening area. However, in the case that the reflection end 12 of the housing 10 has opening(s), the gross opening area of the reflection end 12 is desirable to be less than 75% of the opening dimensional area of open end 13 of the housing 10.

Advantageous Effects of Invention

The respiratory acoustic device 1 of present invention offers an easier method to change the viscosity of mucus in the lungs and airway by artificially vibrating the lungs and the airway of the user. Therefore, anyone can improve the obstruction of the lungs and the airway by removing mucus therein. Also, it offers easy collection of the sputum sample of the diagnostic purpose from the user.

Describing in detail, the respiratory acoustic device 1 of present invention can promote the removal of the mucus from airway and lungs by changing the viscosity of mucus with low frequency acoustic shockwave generated by the Helmholtz resonation between noise produced from a rapid exhalation, i.e. a cough, and the cavity formed by oral cavity and lower respiratory tract. As written above, a living body produces a cough, consciously or reflectively, to improve the obstruction of airway. However, the effect of a cough to remove the viscous mucus in order to clear the airway obstruction could be quite limited because it only functions to shrink the airway and to rapidly exhale the air in the airway by this shrinkage and thus it does not change the viscosity of the mucus and its effect only reaches to the surface of the secretion layer. At this point, focusing on the energy of a cough, it is said that a human consumes roughly 2 kcal of energy per cough. Also, it is said that the airflow speed generated by a cough could be up to more than 160 km/h. Furthermore, a cough is associated with a large noise generated at the airway. If we can convert and utilize even a part of this energy to efficiently vibrate the mucus in the lungs and the airway to promote mucus removal, it would be very effective to improve symptoms of the user.

The respiratory acoustic device 1 of present invention generates the Helmholtz resonation between the noise produced from a rapid exhalation, i.e. a cough, and the cavity formed by oral cavity and lower respiratory tract, by infusing a rapid exhalation by a cough through mouthpiece 20 into a pipe-like shaped hollow housing 10. As the energy of a cough within the noise and exhalation will be directly coupled with the acoustic energy at a very low energy loss, offering enough mucus removal effect even with a very simple and small sized device. That is to say, present invention offers a device with less energy loss, with structurally simple design unlike the conventional respiratory acoustic device (Prior art1) which requires either a separated part like a reed or a metal ball to generate sound or pulse or energy to move the part.

Also, the respiratory acoustic device 1 can provide an acoustical resistance, which is created by composing the flow resistance to blown in the airflow within the device by regulating the diameter, shape of the air passage, and unevenness of the housing 10, to enlarge the virtual volume of oral cavity and lower respiratory tract and as a result, it can support the generation of a lower frequency sound. In the other words, the housing 10 of the current device can be regarded as a port of the loud speaker when considering the cavity formed by oral cavity and lower respiratory tract as a loud speaker enclosure. By applying the acoustic coupling technology based on "Thiele Small" Loud Speaker Parameter, the device can support lower frequency sound over the actual volume of oral cavity and lower respiratory tract. It is possible to enhance the effect to mobilize the mucus by generating low frequency shockwave efficiently under the support from this acoustic resistance to let the cavity formed by the oral cavity and the lower respiratory tract act as it has much higher volume and thus it can resonate with lower frequency sections of the noise of a cough and the noise occurred in the device by a rapid exhalation. Furthermore, the back pressure against the exhalation caused by this acoustic resistance will act to effectively transfer the lower frequency shockwave into the lower respiratory tract. That is to say, the respiratory acoustic device 1 of the present invention can efficiently generate and transmit lower frequency sound shockwave into the airway and lungs by forming acoustic resistance by forming the airflow resistance within housing 10 by its shape.

As mentioned above, the respiratory acoustic device 1 of the present invention can promote mucus removal at a more compact and simpler structure, by generating low frequency sound shockwave by the Helmholtz resonation between the noise produced within housing 10 by a rapid exhalation by a cough and the noise of a cough itself occurred at the airway, and a cavity formed by the oral cavity and lower respiratory tract which act in higher virtual volume under support of acoustic resistance.

DESCRIPTION OF EMBODIMENTS

Following is the description of the exemplary embodiments to apply the present invention. The present invention is not limited to the exemplary embodiments described in the following and includes any suitable modification within the scope of obvious steps. Note that in this description of the present invention, "A-B" means "A or more and B or less".

Figure 1:
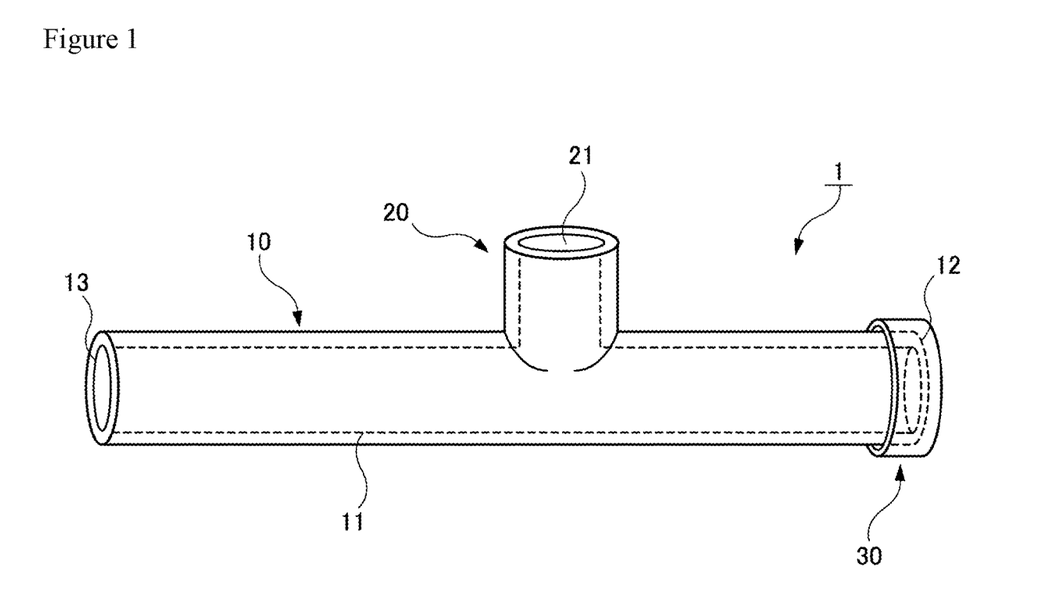
FIG. 1 shows the overall structure of exemplary embodiment of the respiratory acoustic device of the present invention.

FIG. 1 shows an exemplary embodiment of the respiratory acoustic device of the present invention. As shown in FIG. 1, respiratory acoustic device 1 has a housing 10 with hollow space 11 and a mouthpiece 20 which has the air passage 21 which is continuously connected with the hollow space 11. Housing 10 is structured into a cylindrical shape and one end is designed to be a reflection end 12 where the airflow blown in from mouthpiece 20 reflects and the other end is designed to be an open end 13 where the airflow blown in from mouthpiece 20 exits. The reflection end 12 is an end section of housing 10 where a cap which is sealed or with small opening(s) is located to produce the reflection of the airflow by obstructing the airflow. The open end 13 is an end section of housing 10 where there is no obstructing component of the airflow. In this exemplary embodiment, a removable cap 30 is attached at the reflection end 12 of housing 10. The cap 30 does not have any openings and completely seals reflection end 12 when attached to housing 10.

In this embodiment, in the tubular housing 10, the hollow space 11, which is connecting reflection end 12 and open end 13, is linearly formed and the mouthpiece 20 is located between said reflection end 12 and open end 13. Also, the mouthpiece 20 is disposed to housing 10 in condition that the angle between the center axis of hollow space 11 of housing 10 and the center axis of air passage 21 of mouthpiece 20 is approximate right angle (85-95 degree). As shown in FIG. 1, it is desirable that the connecting point of mouthpiece 20 and housing 10 is shifted (offset) from the center of length of housing 10. In detail, in the exemplary embodiment shown in FIG. 1, the length between mouthpiece 20 and the reflection end 12 of housing 10 is set to be shorter than the length between mouthpiece 20 and the open end 13 of housing 10. By this feature, the blown in airflow at the mouthpiece 20 will split apart into two directions in housing 10 and arrive and cause an airflow reflection at the reflection end 12 earlier than the airflow discharge at the open end 13, causing a larger flow resistance and enhancing the effect of the acoustic resistance.

In this embodiment, the housing 10 and the mouthpiece 20 are integrally formed of a single material and the cap 30 is solely designed as a separated part. The selection of material for housing 10, mouthpiece 20, and cap 30 can vary from, resin like plastics, paper or wood, combustible material like non-woven fabric, glass and metal, according to the cost and applications as long as it is less air permeable and can generate an airflow into the housing 10.

Figure 2:
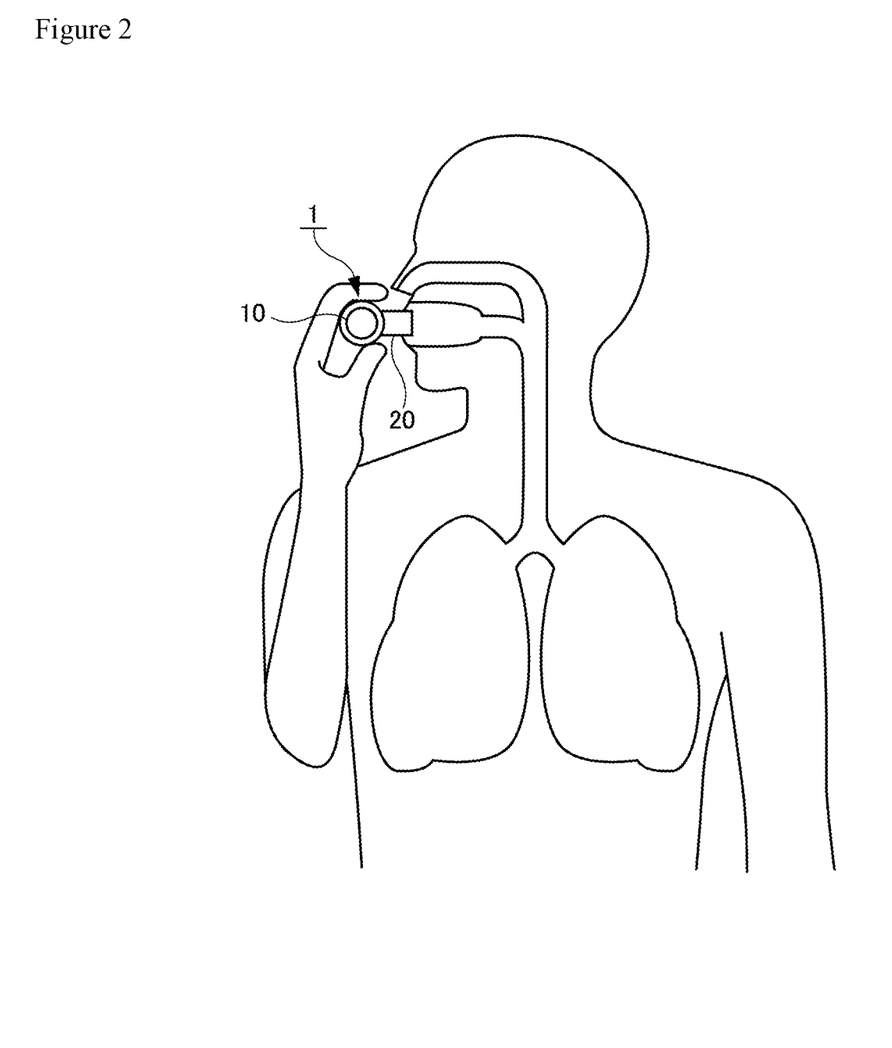
FIG. 2 shows a simplified method of application of the respiratory acoustic device.

FIG. 2 is the simplified drawing of exemplary method of application of the respiratory acoustic device 1. As shown in FIG. 2, the user holds the housing 10 (desirably by both hands) and blow air into the mouthpiece 20 by the rapid exhalation, i.e. cough while his mouth is holding the mouthpiece. The airflow, blown into the housing 10 from the mouthpiece 20, goes through the air passage 21 of the mouthpiece 20 and hits the inner wall surface of the hollow space 11 of the housing 10, then splits apart into two directions. The noise will be produced by the airflow vibration which was caused by the friction with the inner surface of the housing 10, also, by the vortex produced by the redirected airflow along with the device shape being collided at the convex sections of the connecting point of housing 10 and mouthpiece 20. As described above, the connecting point of housing 10 and mouthpiece 20 is offset from the center and one end of the housing 10 is the reflection end. As the result, the airflow reflects into the inside of hollow part 11 as it will be dammed at reflection end 12, then heading to the open end 13 of the other end. This limitation of the flow passage by the reflection end 12 produces resistance to the airflow blown into housing 10 and this acts as the acoustic resistance. Also, the shape of this housing 10 makes the cavity formed by the oral cavity and the lower respiratory tract act as it has larger virtual volume thus supporting the lower frequency acoustic energy. Additionally, it is possible with the present invention to realize a higher resistance to the airflow by embedding roughness to the inner surface of the hollow space 11 of the housing 10. Furthermore, the back pressure to the exhalation produced by this acoustic resistance makes lower frequency acoustic shockwave to efficiently transfer to the lower respiratory tract.

It is possible to extend the virtual length of the port (the neck section: length "l" of the FIG. 4) which is the influence element of the resonance effect for the generation of the Helmholtz resonation by the disposing reflection end 12 to the housing 10, because the airflow blown in from mouthpiece 20 take a path to goes through reflection end 12 before exits from open end 13. This will enable it to generate lower frequency resonance. Also, the disposing reflection end 12 improves sealability inside of the housing 10 thus giving higher pressure and airflow speed inside the device with more complicated air passage within the pipe, as a result, a louder noise will be produced by the generated vortex. The noise generated in the device as described above and the noise of the cough itself generated at the airway will act as the factor to generate a Helmholtz resonation with the cavity formed by oral cavity and lower respiratory tract.

As described above, the respiratory acoustic device 1 of the present invention is possible to promote the removal of mucus that is outside of the airway by liquidating the airway secretion by generating low frequency acoustic shockwave, which is produced by the Helmholtz resonation between, the noise of a cough itself that occurred at the airway and the noise occurred in the housing 10 by a rapid exhale of the cough, and the cavity formed by the oral cavity and lower respiratory tract, which act as it has higher virtual volume because of the structured acoustic resistance.

At this point, the peak of the low frequency acoustic shockwave coupled by Helmholtz resonation is desirable to be around 18 Hz of the cilia beating frequency but it does not have to be exactly the same. For example, if low frequency sound of 16 Hz-25 Hz is generated, the harmonics effect will promote the effective vibration as of cilia beating frequency to the airway and the lungs.

Figure 3:
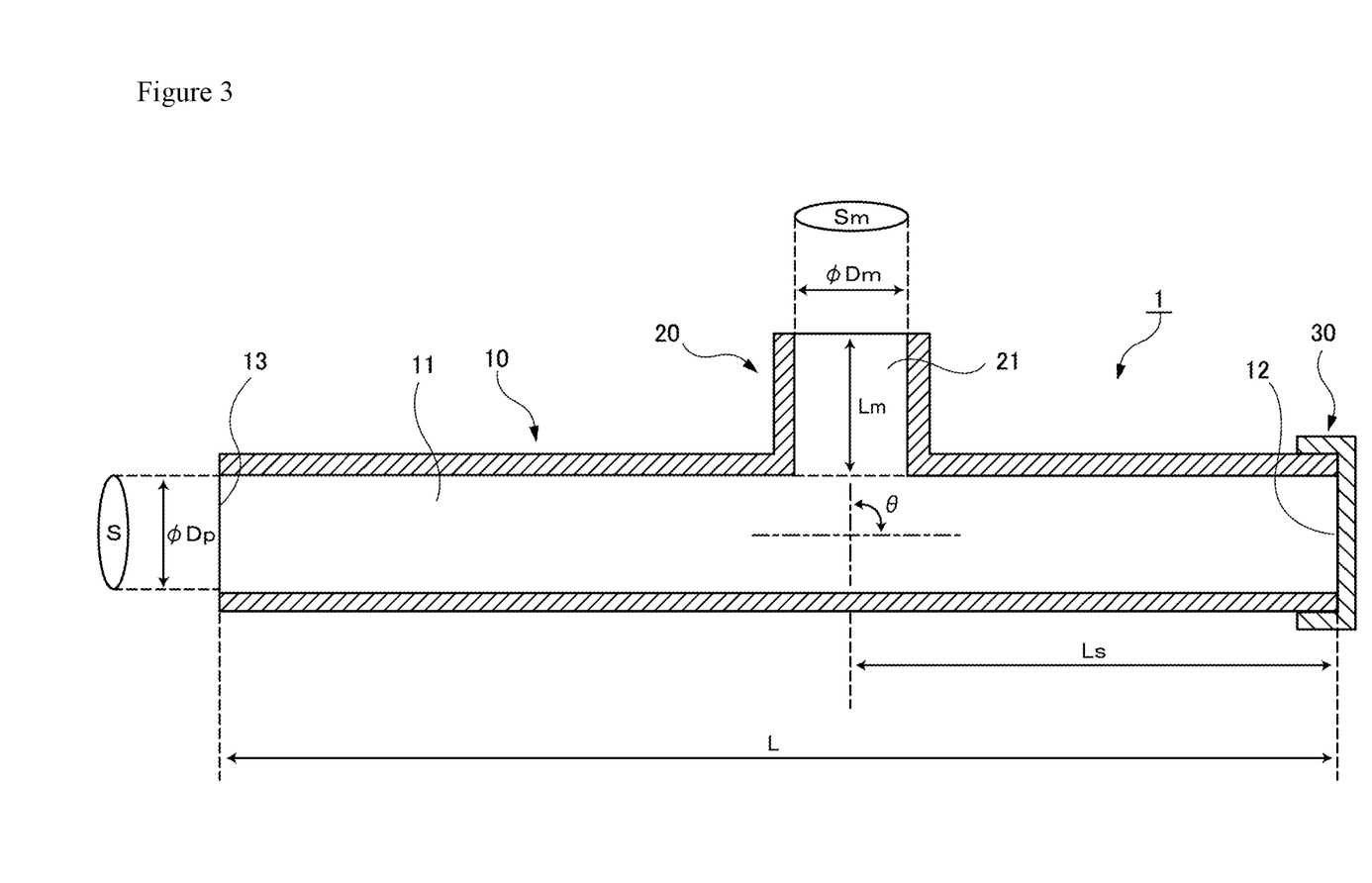
FIG. 3 shows a dimensional structure of respiratory acoustic device of one embodiment of present invention.

FIG. 3 shows the dimensional structure of the respiratory acoustic device 1. The desirable exemplary dimensions of the respiratory acoustic device 1 is described with in the following. Note that each dimension is not limited to that of the following description.

At first, the size of the air passage 21 of the mouthpiece 20 should be large enough to blow in a rapid exhale into the housing 10 without being a burden to the user. In detail, it is desirable that the diameter $\varphi Dm$, of the air passage 21, when dimensional shape of the passage 21 of the mouthpiece 20 is circular, is desirable when around 5-25 mm but, 10-20 mm would be more desirable. Also, it is desirable that dimensional area Sm of the air passage 21 of the mouthpiece 20 is 0.64-9 $cm^2$ but, 0.80-5 $cm^2$ would be more desirable. Especially, it would be optimal to set the inner dimension area Sm of the air passage 21 to 1-2 $cm^2$, which is approximately the same as a human airway's dimension size. It is possible to give pressure vibration like spring to the air within the oral cavity and lower respiratory tract by designing the air passage 21 of mouthpiece 20 to the above range. This also allows the efficient transfer of the low frequency shockwave because the back pressure caused by the acoustic resistance can reach to the lower respiratory tract. More desirably, it would be possible to secure the size of the air passage 21 to have said effect by keeping the dimensional widths of the air passage 21 to be more than 8 mm.

It is desirable in the respiratory acoustic device 1 of the present invention to design the dimension of air passage 21 of the mouthpiece 20 and the dimension of the hollow space 11 of the housing 10 to be the same. In detail, at least, the dimension area Sm of the air passage 21 of the mouthpiece 20 and the dimension area S of the open end of the housing 10 to be equal, and the diameter $\varphi Dm$ of the air passage 21 of the mouthpiece 20 and the diameter $\varphi Dp$ of the open end of the housing 10 to be equal. By this design, the respiratory acoustic device 1 can effectively offer the function to vibrate the air inside by acting as a continuous port for the Helmholtz resonation. Additionally, by making the air passage 21 of the mouthpiece 20 and hollow space 11 of the housing 10 to be the same dimension, the whole device can be manufactured with a simple process using few kinds of materials. For example, it is possible to build the current device easily by cutting a single pipe into two parts and drilling a hole to one part and inserting the other part into the hole. It is also possible to realize a mass production of the current device in a low cost if the air passage 21 and the hollow space 11 is the same dimension. It is assumed to hire this type of production method especially in low resource countries.

It is desirable that the inner dimensional area S of the open end 13 of the housing 10, and the length l of the passage inside the device which the blown in airflow from mouthpiece 20 exit from open end 13 after reflected at the reflection end, to be designed to meet with the following formula. Note that the passage 1 in the device is the total value of, length Lm of the air passage 21 of the mouthpiece 20, length Ls of the mouthpiece 20 to the reflection end 12 of the housing 10, length L of the reflection end 12 to the open end 13 of the housing 10. (l=Lm+Ls+L)

$$f = \frac{c}{2\pi}\sqrt{\frac{S}{Vl}}$$ [Formula]

At this formula, the calculation should be done under following numbers and ranges: f is the frequency, 16-25 Hz, c is the sonic speed, 35000 cm/s, and V is the total lung capacity of the lungs, 1500-9000 ml.

Figure 4:
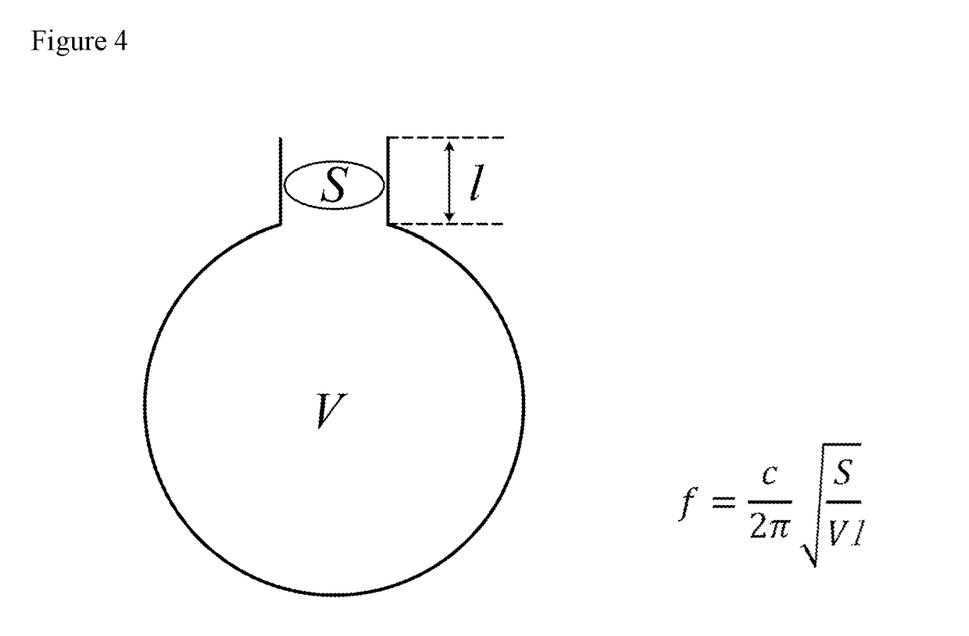
FIG. 4 shows a standard formula of resonance frequency of Helmholtz resonation.

The above formula is a general formula for calculation of the frequency of Helmholtz resonation and the port length structured by the current device (l=Lm+Ls+L) and the total lung capacity V shall be applied. However, as it is not under consideration of elements of the material of the cavity of the lower respiratory tract or the virtual volume increased by the acoustic resistance etc., it is not offered as the calculation of the frequency of the generated low frequency shockwave in reality but as a summarized range of the dimension of the shape of the device. We regard it as appropriate to refer this dimension range under the above formula for the design of the device shape, according to the basic concept of the present invention of resonating the noise of the cough to the cavity of the lower respiratory tract. Note that FIG. 4 is showing the general formula of the Helmholtz resonation. As shown in FIG. 4, at a container which has an opening, V is the total volume of the container, S is the dimension area of the opening, l is the length of the port to connect to the inside of the container. If these V, S, and l are settled, the frequency of Helmholtz resonation f generated from this container can be calculated.

For example, assume that the user is a small child whose total lung capacity V is 2400 cm², the inner dimension area S of the open end 13 of the housing 10 is 1 cm², the inner dimension are Sm of the air passage 21 of the mouthpiece 20 is the same area, the length of the passage 1 of the device is 33 cm, the resonance frequency generated from Helmholtz resonation calculated from the above formula is 19.793 Hz (sonic speed c set to be 35000 cm/s). In this way, even a small child can easily generate a low frequency wave to promote the removal of the airway mucus by utilizing the respiratory acoustic device 1 of the present invention.

Note that in FIG. 3, the length from mouthpiece 10 to the reflection end 12 of the housing 10 is indicated as letter Ls and the length from the reflection end 12 to the open end 13 of the housing 10 indicated as letter L. As described above, it is desirable that the distance from mouthpiece 20 to the reflection end 12 of the housing 10 is set to be shorter than the distance from mouthpiece 20 to the open end 13 of the housing 10. In detail, it is desirable that the length Ls between mouthpiece 20 and reflection end 12 is 10-45% of the total length of the housing 10, and 15-40% would be more desirable. From this design, the airflow blown in through mouthpiece 20 can reach to the reflection end 12 earlier than its exit from the open end 13 of the housing 10 and causes the airflow reflection.

Also, in FIG. 3 of the letter θ indicate the angle between the center axis of the air passage 21 of the mouthpiece 20 and center axis of the hollow space 11 of the housing 10, and the angle of the reflection end 12. The angle θ is desirable to be 90 degree, but is acceptable to be the within the range of 70-110 or 80-100 degree. Additionally, to let the blown in airflow go through mouthpiece 20 to reach earlier to the reflection end 12 than to the open end of housing 10, the angle θ may be more than 90 degree. For example, the angle θ may be 95-130 degree or 100-120 degree.

Figure 5:
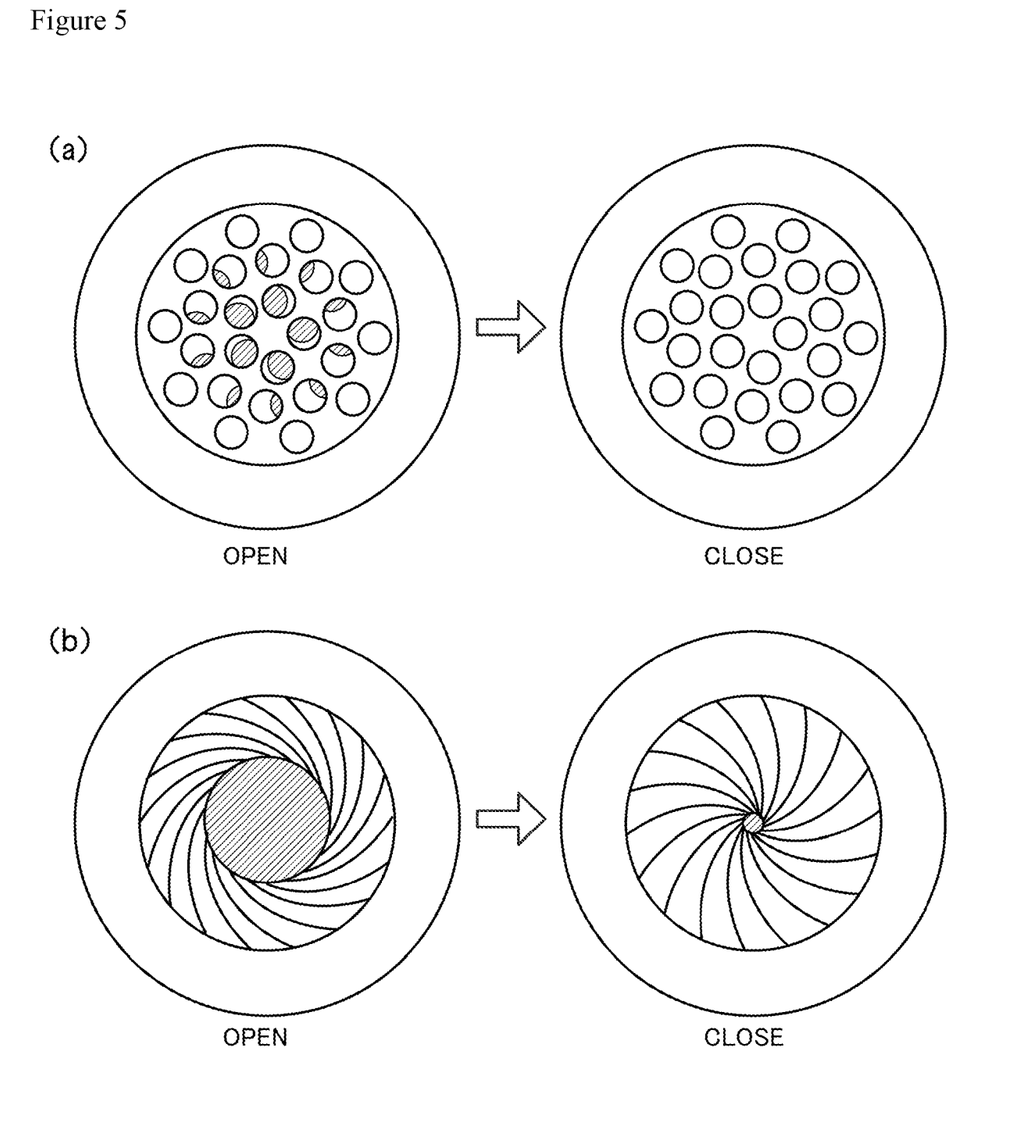
FIG. 5 shows an example of the reflection end where regulation of the open area is possible.

FIG. 5 is the modified example of the reflection end 12 of the housing 10. In the exemplary embodiment shown in FIG. 5, the reflection end 12 of housing 10 has one or more openings and it is with the feature to regulate the opening area.

In detailed description, in an example of FIG. 5(a), the reflection end 12 is structured by overlapping two cap parts, each of them has plural holes. Then, turning one of the two cap part relatively, causes the openings to the inside of the housing 10 to open up when the position of the holes of both cap parts are corresponded and the openings to the inside of the housing 10 closes when the position of the holes of both cap parts are inconsistent. Additionally, it is possible to make slight adjustments of the area of the openings by controlling the turning angle of the cap part.

In the exemplary embodiment shown in FIG. 5(b), the reflection end 12 is composed with the mechanism like diaphragm blades of camera. In this mechanism, the plural blades parts are located around the opening and the opening is closed when each blade part extends to the center of the opening and the opening is extended when each blade part slides back to the outside edge of the reflection end 12. It also designed to make slight adjustments of the opening area by the extension amount of each blade part.

However, there is a possibility of a dilution of the effect of obstructing and reflecting the airflow by the reflection end 12 if there are one or plural openings at the reflection end, thus unable to generate an effective low frequency acoustic shockwave to the lungs and the airway by the current device. To avoid this, it is suitable to limit the total opening area of the reflection end 12 to be less than 75% to the opening area of the open end 13 and more desirably, less than 50% or less than 30%.

As described above, it is possible to make slight adjustments to the resonance frequency of the respiratory acoustic device 1 by disposing opening(s) at the reflection end 12 or disposing mechanism to adjust the opening area. Also, this feature regulates the resistance to the exhalation and makes airflow input easier. Therefore, it is possible to adjust the working respiratory pressure of the device and the resonance frequency to achieve proper function and effect, according to the age, respiratory function, and symptoms of the user, by adjusting the opening area of the reflection end 12.

As in the above description of the present application, we described about exemplary embodiments referring to figures to express contents of the present invention. However, the present invention is not limited to the said exemplary embodiments described above and includes any modified formation or improved formation within the scope of the obvious steps based on the contents written in this description of the present application.

For example, it is possible to structure the respiratory acoustic device 1 to a foldable configuration, or to be able to separated and reassembled. Also, it is possible to make the whole device disposable by composing it with a single material or more than a few materials combined, or making a part of the device (i.e. mouthpiece 20) disposable. Additionally, to make it easy-to-wash after usage, the design to open up the housing 10 may be possible.

INDUSTRIAL APPLICABILITY

The respiratory acoustic device of the present invention is to improve the clearance of the mucus in the lower respiratory tract by the above described method to generate low frequency acoustic shockwave in the airway and the lungs, and has potential to be applied to multiple fields. That is, by applying the present invention, it is possible to improve the respiratory function by resolving the disease related obstruction of the lower respiratory tract by promoting the removal of the mucus. Also, it prevents the exhaustion of the patient and the exacerbation by bringing antitussive effect as a result of the improvement of the lower airway obstruction. Additionally, it is possible to contribute to the acute diagnosis of tuberculosis and lung cancer by supporting the sputum sampling of the lower respiratory origin by inducing sputum from the patient. It is also effective to prevent accidents like pneumonia caused by poor sputum clearance or like atelectasis. Even for the healthy individuals, it is possible to improve their performance and safety by improving the respiratory function by promoting the removal of the airway mucus using the respiratory acoustic device of the present invention, in such occasions like before an exercise, before playing a wind instrument, before singing, or trekking a high mountain where air is thin.

REFERENCE SIGNS LIST

1 . . . Respiratory acoustic device
10 . . . Housing
11 . . . Hollow space
12 . . . Reflection end
13 . . . Open end
20 . . . Mouthpiece
21 . . . Air passage
30 . . . Cap

The invention claimed is:

1. A respiratory acoustic device comprising a housing with a hollow space, and a mouthpiece which has an elongated cylindrical shape including an air passage connected with the hollow space,
   wherein the mouthpiece is configured to be able to receive an exhalation while being held by a user's mouth from outside of a side wall of the mouthpiece and fully inserted an opening end of the mouthpiece in the user's mouth,
   wherein the housing contains:
      a reflection end which reflects an airflow of the exhalation blown from the mouthpiece, and
      an open end which outputs the airflow of the exhalation blown from the mouthpiece,
   wherein the housing is tubular that one end is the reflection end and the other end is the open end,
   wherein the mouthpiece is located between the reflection end and the open end of the housing,
   wherein the mouthpiece is configured such that a center axis of the air passage cross with an inner wall of the hollow space of the housing,
   wherein the device is configured to generate the Helmholtz resonation between a noise produced from the exhalation and a cavity formed by the user's oral cavity and lower respiratory tract by infusing the exhalation through the mouthpiece into the housing,
   whereby the device is further configured to create an acoustic resistance to the airflow of the exhalation blown into the housing through the mouthpiece, and so that back pressure against the exhalation caused by the acoustic resistance transmits a low frequency sound shockwave into the user's lower respiratory tract through the mouthpiece, and
   wherein the device does not comprise a part that moves with exhalation blown from the mouthpiece.

2. A respiratory acoustic device according to claim 1, wherein the housing is configured such that the hollow space connecting the reflection end and the open end is linear.

3. A respiratory acoustic device according to claim 1, wherein an inner dimension area of the air passage of the mouthpiece is 0.64 to 9 cm$^2$.

4. A respiratory acoustic device according to claim 3, wherein a difference between the inner dimension area of the air passage of the mouthpiece and an inner dimension area of the hollow space of the housing is within ±5%.

5. A respiratory acoustic device according to claim 1, wherein an inner dimension area S[cm$^2$] of the open end, the total length l [cm] of the passage in the device, the airflow of the exhalation blown from the mouthpiece being reflected at the reflection end and outputted from the open end, satisfy the following formula, $$f = \frac{c}{2\pi}\sqrt{\frac{S}{Vl}} \quad \text{(Formula)}$$

Wherein f is to be frequency of 16-25 Hz, c is to be sonic speed of 35000 cm/s, and V is to be the Total Lung Capacity of 1500-9000 ml.

6. A respiratory acoustic device according to claim 1, wherein the reflection end has no opening, or with one or more openings, or with a mechanism to adjust the opening area, and
   wherein a total opening dimensional area of the reflection end is less than 75% of an opening dimensional area of the open end.

* * * * *